United States Patent [19]
Hewitt et al.

[11] Patent Number: 5,090,907
[45] Date of Patent: Feb. 25, 1992

[54] DENTAL CURETTE WITH FINGER PAD

[76] Inventors: Fred G. Hewitt, 545 Chapel La., Eagan, Minn. 55121; John C. Conrad, 4729 Covington Ct., Eagan, Minn. 55122; Kathy J. Conrad, 4729 Covington Ct., Eagan, Minn. 55122

[21] Appl. No.: 746,606

[22] Filed: Aug. 19, 1991

[51] Int. Cl.$^5$ .............................................. A61C 3/02
[52] U.S. Cl. .................................. 433/144; 433/141; 433/143
[58] Field of Search ............... 433/144, 143, 141, 164

[56] References Cited
U.S. PATENT DOCUMENTS

| | | | |
|---|---|---|---|
| 1,707,952 | 4/1929 | Schneider | 433/144 |
| 1,844,913 | 2/1932 | Hallowell | 433/144 |
| 3,721,006 | 3/1973 | Malmin | 433/141 |

FOREIGN PATENT DOCUMENTS 74225 12/1866 United Kingdom ............... 433/144

Primary Examiner—John J. Wilson
Attorney, Agent, or Firm—Haugen and Nikolai

[57] ABSTRACT

A dental curette or scaler having a finger pad including a generally concave finger surface proximate a working head and complementary contoured to the shape of an extended middle finger urged thereupon. The finger pad is selectively rotatable about and removable from a tapered end closely proximate the working head of the instrument. The finger pad is comprised of a resilient material to adapt to individual finger variations and is textured to provide a comfortable feel and a friction grip to the dental hygienist or dentist. The finger pad is restricted from lateral sliding along a longitudinal axis of the instrument and, further, is sterilizable prior to use. In an alternative embodiment of the invention, the finger pad has a plurality of finger surfaces for receiving a finger in more than one position.

23 Claims, 4 Drawing Sheets

DENTAL CURETTE WITH FINGER PAD

BACKGROUND OF THE INVENTION

I. Field of the Invention

This invention relates generally to dental instruments used by dentists and dental hygienists for treatment of teeth and, more particularly, to a dental curette or scaler having a sharpened working end.

II. Discussion of the Prior Art

Present day dental instruments including dental curettes typically comprise of a shaft member having a tapered portion extending to a sharpened working end. A typical dental curette known in the art, as shown in FIG. 1, is shown to illustrate the tapered portion proximate the sharpened working end. Dental instruments, such as the instrument shown in FIG. 1, are typically held by the hand with the tip of the middle finger pressed upon the tapered portion to apply pressure when maneuvering the instrument against a patient's teeth. When the user's middle finger is pressed upon this tapered portion, a substantially large amount of pressure is exerted on a relatively small surface area of the middle finger due to the small contact area with the tapered portion of the instrument. Extended periods of use of the instrument with the substantially large pressure exerted on the small surface area of the middle finger can result in a variety of tissue, muscle and nerve damage. This concentrated pressure can also aggravate and contribute to accumulative trauma such as tendonitis, tenosynovitis and/or cause carpal tunnel syndrome.

OBJECTS

It is accordingly a principal object of the present invention to provide an ergonomically improved dental instrument which substantially reduces the large amount of pressure concentrated on a small surface area of the finger engaging the dental instrument. Another object of the invention is to provide a dental instrument having an improved head area for comfortably receiving the middle finger and which is selectively rotatable to accommodate the middle finger in a comfortable position.

Another object of the invention is to provide an instrument having a finger pad which is detachable and sterilizable.

SUMMARY OF THE INVENTION

The foregoing features and objects of the invention are achieved by providing a dental curette having a finger pad member axially constrained proximate the working end for comfortably receiving the extended middle finger by distributing pressure upon a greater surface area of the finger. The dental curette is adaptable to be held by the hand of a user and comprises an elongated shaft member having a first end and a second end tapering toward the working end wherein the finger pad is complementary contoured to comfortably receive the middle finger.

A further improvement of the invention includes a finger pad wherein the contoured finger surface is generally concave to receive the middle finger. Further, the finger pad can be fixedly attached or selectably rotated about an axis of the shaft member. This rotatability feature allows the user to selectively position the finger pad for a comfortable orientation while in use.

A further improvement of the invention includes a groove or a ridge arcuately disposed about a mid-portion of the tapered second end for restraining lateral sliding of the finger pad along an axis of the curette.

A further improvement of the invention includes a finger pad having a plurality of generally concave finger surfaces for providing alternate sites for positioning a finger on the dental curette.

Other objects and improvements of the invention will become apparent to the reader in the foregoing discussion.

The foregoing features, objects, and advantages of the inventions will become apparent to those skilled in the art from the following detailed description of a preferred embodiment, especially considered in conjunction with the accompanying drawings in which like numerals in the several views refer to corresponding parts.

DESCRIPTION OF THE PREFERRED EMBODIMENT

Figure 1:
FIG. 1 shows a profile view of the prior art.
Figure 2:
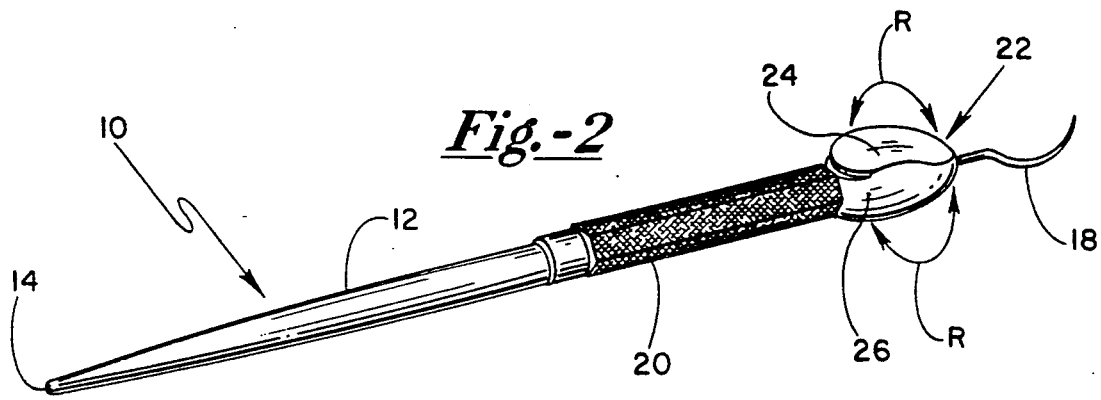
FIG. 2 shows a perspective view of the invention including a finger pad member proximate the working head of the instrument.

FIG. 2 is a perspective view of a dental scaler 10, which could also be a dental curette or similar instrument and is referred to generally as a dental curette throughout, comprising an elongated generally cylindrical shaft member 12 having a tapered first end 14 and a shank or second end 16 (hidden in this figure) tapering to working member 18. Metal shaft member 12 also includes a knurled textured segment 20 nearly proximate second end 16 which is gripped by the hand of a user. A finger pad member 22 having a generally elliptical and concave finger receiving surface 24 complementary to the curvature of a finger is coaxially constrained about second end 16. Finger pad 22 is comprised of a resilient material such as silicone rubber or plastic for a comfortable feel and conforming to finger variations. Finger surface 24 is textured providing a slip resistant and friction grip, such that the finger engaging finger surface 24 does not slide easily when gripping curette 10. Finger pad 22 has a rounded second surface 26 comprising the remainder of the outer surface of finger pad 22, wherein second surface 26 increasingly tapers towards sharpened member 18.

When curette 10 is held in a modified pen grasp by a hand of the user, the palm of the hand engages curette 10 such that a pad area of the fingers grip knurled area 20 wherein the middle finger extends towards sharpened member 18 and comfortably engages concave finger surface 24. Finger surface 24 is complementary contoured to the curvature of the middle finger of the user to comfortably receive the pressing middle finger when curette 10 is maneuvered against a patient's teeth. During normal use the middle finger comfortably engages finger surface 24 such that substantially even pressure is distributed upon the surface of the middle finger. Finger pad 22 is located in a close proximity to and rotatably adapted about a longitudinal axis of shaft 12 such that finger pad 22 can be selectively positioned with a substantially small torque. This arrangement allows member 18 to properly engage teeth of a patient while the user's hand and fingers remain comfortably positioned while holding curette 10. Finger pad 22 may also be fixedly attached to second end 16 if desired.

Figure 3A:
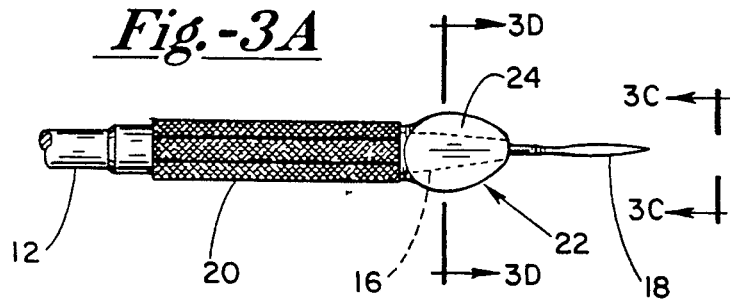
FIG. 3A shows a top view of the finger pad member according to the invention.

Referring to FIG. 3A, a partial top view of curette 10 shown in FIG. 2 is shown. Finger pad 22 is generally oval having an generally elliptical and concave finger surface 24 as shown. The major axis of the elliptical finger surface 24 is generally aligned with the longitudinal axis of shaft member 12.

Figure 3B:
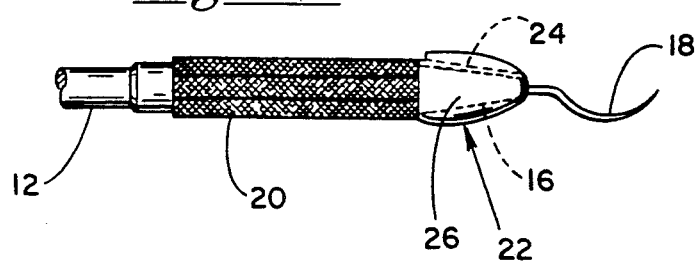
FIG. 3B shows a side view of the finger pad member according to the invention.

Referring to FIG. 3B, a side view is shown of finger pad 22 disposed about second end 16 of shaft member 12. Finger surface 24 gradually tapers toward member 18 and a longitudinal axis of shaft member 12 such that the middle finger engaging finger surface 24 forms an acute angle relative to the longitudinal axis of shaft member 12.

Figure 3C:
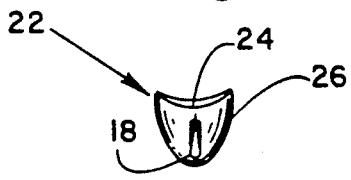
FIG. 3C shows a front view 3C—3C of the finger pad member according to the invention.

Referring to FIG. 3C, a front view of finger pad 22 is shown to further illustrate tapered and curved finger surface 24.

Figure 3D:
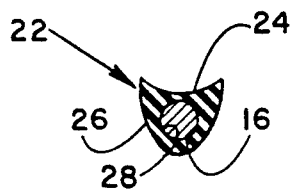
FIG. 3D shows a front sectional view 3D—3D of the finger pad member shown in FIG. 3A.

Referring to FIG. 3D, a sectional view of Section 3D—3D as shown in FIG. 3A is shown to illustrate finger pad 22 rotatably disposed about second end 16. Finger pad 22 has a generally conical inner surface 28 complementary adapted to tapered second end 16 and substantially encompassing a circular periphery of second end 16.

Figure 4A:
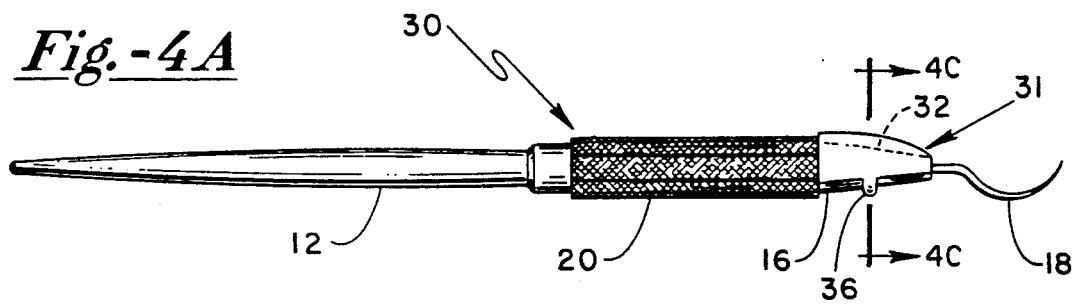
FIG. 4A shows a profile view of a detachable finger pad member according to an alternative embodiment of the invention.

Now referring to FIG. 4A, an alternative embodiment of the invention is shown generally at 30. Finger pad 31, having a generally concave and tapered finger pad surface 32 similar to finger surface 24 as previously discussed and shown in FIG. 2, is illustrated where finger pad 31 is selectively detachable and mountable to tapered second end 16 without removing member 18.

Figure 4B:
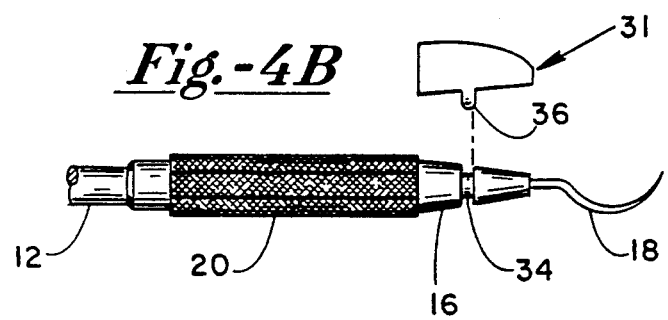
FIG. 4B shows an exploded view of the finger pad member according to FIG. 4A.

Referring to FIG. 4B, an exploded view of FIG. 4A is shown wherein tapered second end 16 has an arcuate continuous groove 34 located about a periphery of a midsection of tapered second end 16. Finger pad 31 has a generally conical and arcuate inner surface 33 complementary to interfacing tapered second end 16 for a snug fit. Groove 34 receives two arcuate and pliable clip fingers 36 of finger pad 31 in a friction fit to prevent lateral sliding of finger pad 31 along a longitudinal axis of tapered second end 16. Groove 34 could also extend less than 360° to restrict the rotation angle of engaged fingers 36 such that rotation of finger pad 22 is restricted to less than 360°.

Figure 4C:
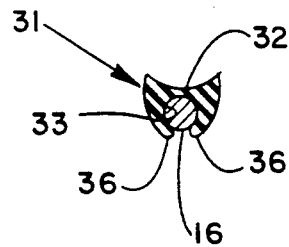
FIG. 4C shows a sectional view 4C—4C shown in FIG. 4A.

Referring to FIG. 4C, section 4C—4C of FIG. 4A is shown to illustrate fingers 36 each oppositely opposed of one another and wrapped around tapered second end 16 to snugly secure and clamp onto second end 16. Finger pad 31 is constructed of resilient material similar to finger pad 22 such that fingers 36 can stretch outward and away from second end 16 when finger pad 31 is selectively removed from second end 16.

Figure 5:
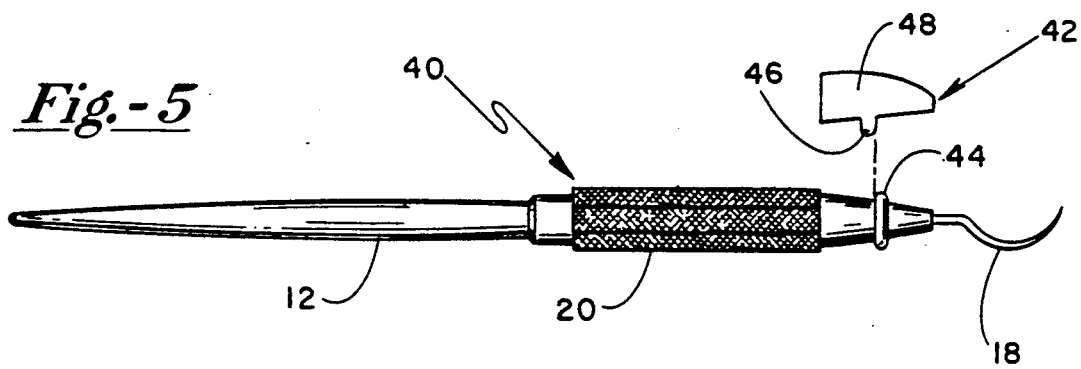
FIG. 5 shows an exploded view of another alternative embodiment of a detachable finger pad member.

Referring to FIG. 5, a further alternative embodiment is shown generally at 40 having a finger pad 42 wherein a midsection of tapered second end 16 includes a rounded ridge portion 44 arcuately protruding above the surface of tapered end 16. Similar to fingers 36 in FIG. 4B, arcuate and pliable clip fingers 46 each snap over and wrap around tapered second end 16 to form a snug fit. Here, fingers 46 are each disposed between knurled area 20 and ridge portion 44 such that ridge portion 44 is complementary received in contoured groove 48 arcuately disposed in an arcuate inner surface (not shown) of finger pad 42 which restricts finger pad 42 from laterally sliding along the longitudinal axis of tapered second end 16. Finger pad 42 is also selectively rotatable about second end 16.

Figure 6A:
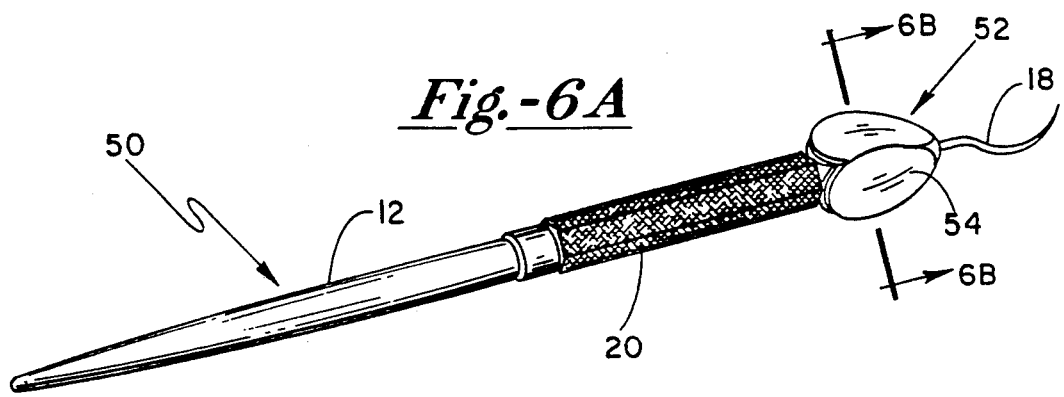
FIG. 6A shows a perspective view of an alternative embodiment of the invention having more than one finger surfaces.
Figure 6B:
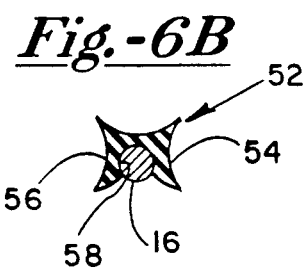
FIG. 6B shows a sectional view 6B—6B shown in FIG. 6A.

Referring to FIG. 6A, another alternative embodiment is shown generally at 50 wherein a variation of finger pad 42 is shown as finger pad 52 including two finger surfaces 54 and 56 for receiving a middle finger providing two finger positions. Similar to finger pad surface 42, finger pad surfaces 54 and 56 are each generally concave having a generally elliptical periphery and adapted to provide alternate sites for the user's middle finger. Referring to FIG. 6B, finger pad 52 has a tapering, arcuate inner surface 58 which is complementary to and also selectively removable from tapered second end 16 in a manner similar to finger pad 31 illustrated in FIG. 4C.

Figure 7A:
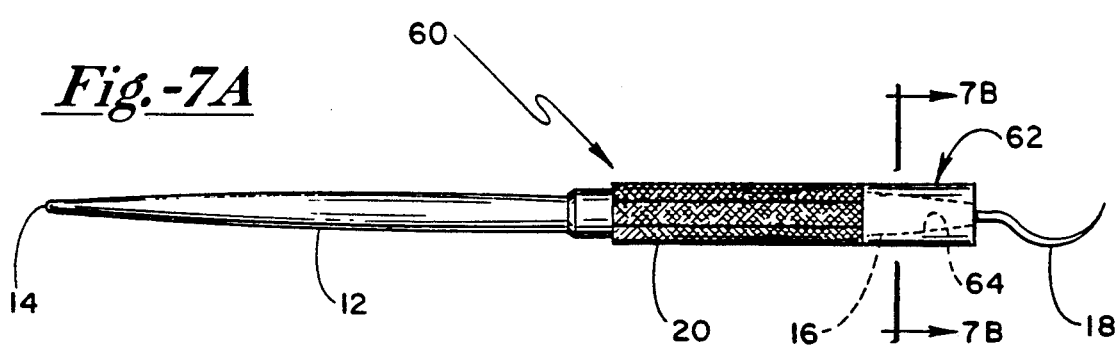
FIG. 7A shows a profile view of an alternative embodiment of the finger pad member having a generally cylindrical finger pad member.
Figure 7B:
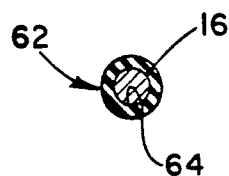
FIG. 7B shows a sectional view 7B—7B shown in FIG. 7A.

Referring to FIG. 7A, an alternative embodiment of the invention is shown generally at 60 wherein generally cylindrical finger pad 62 having a diameter substantially equal to a diameter of knurled area 20 is axially constrained and rotatably adapted about tapered second end 16 in a manner similar to finger pad 22 shown in FIG. 2. Finger pad 62 also comprises a resilient and textured material similar to that of finger pad 22 for comfortably receiving the middle finger of a user. The length of finger pad 62 is sufficiently long to provide sufficient large contact area with the middle finger of user to distribute pressure. As shown in FIG. 7B, rotatable finger pad 62 has a tapered inner surface 64 conforming closely to interfaced tapered second end 16 of shaft member 12.

Member 18 is removable from shaft 12 to allow insertion and replacement of finger pads 22, 52 and 62. Each finger pad is sterilizable along with shaft member 12.

Figure 8A:
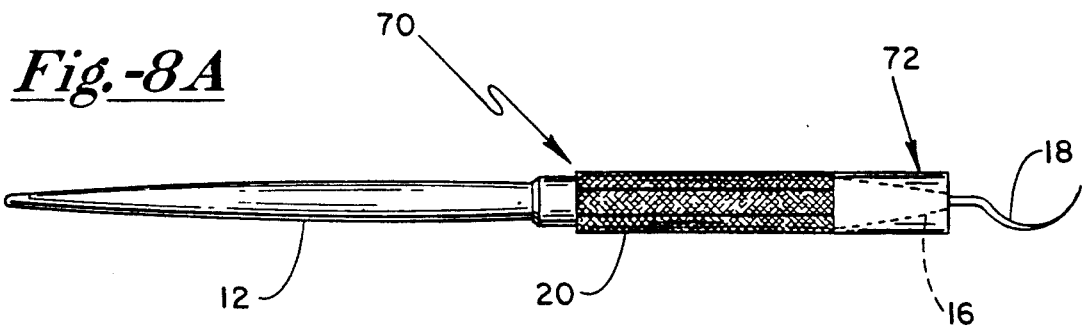
FIG. 8A shows a profile view of another alternative embodiment of a sleeve-like finger pad member.
Figure 8B:
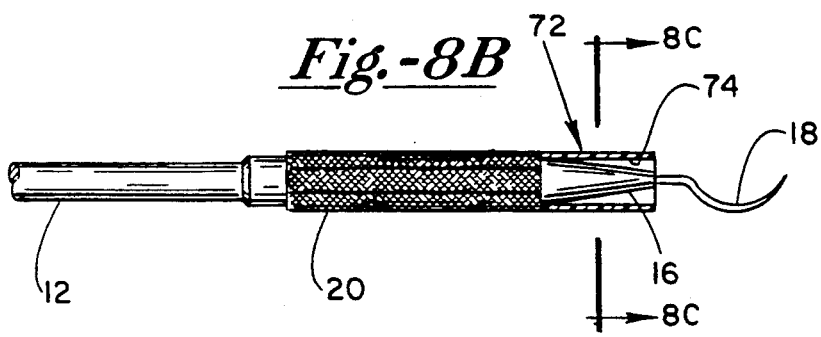
FIG. 8B shows a partial longitudinal sectional view of sleeve-like finger pad member shown in FIG. 8A.
Figure 8C:
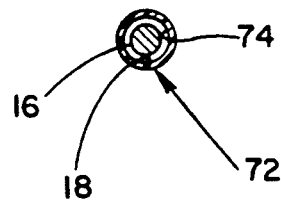
FIG. 8C shows a cross-sectional view 8C—8C shown in FIG. 8A.

Referring to FIG. 8A, another alternative embodiment of the invention is shown generally at 70 wherein a deformable tubular sleeve 72 is axially disposed over tapered second end 16 in an interference fit providing a larger surface than second end 16 to distribute finger pressure and comfortably receive fingers of a user. As shown in FIG. 8B, sleeve 72 has a sufficiently thin wall thickness such that sleeve 72 is flexible. Sleeve 72 has an inner surface 74 having a first portion frictionally engaging the thickest portion of second end 16 and a second portion standing off of tapered second end 16 proximate member 18 such that sleeve 72 can be squeezed and selectively attached to curette 10 without removing member 18. Sleeve 72 has a diameter substantially equal to the diameter of knurled area 20. Sleeve 72 could also have a tapered, generally conical shape tapering toward member 18. Sleeve 72 has a length sufficiently long to securingly engage tapered second end 16, providing a sufficiently large surface area to receive a finger, while leaving member 18 sufficiently exposed. Sleeve 72 is also textured to provide a secure grip. FIG. 8C shows a cross-sectional view of sleeve 72 standing off from second end 16.

In summary, the invention disclosed includes a finger pad which is axially disposed over a tapered second end of a shaft member of a dental curette proximate the working end of the instrument. The finger pad contoured to comfortably receive a finger distributing pressure and is selectively rotatable about a shaft axis. Further, the finger pad is detachable, sterilizable, textured and resilient. While the second end 16 of the shaft member 12 has been illustrated as tapered, limitation to such a shape is not to be inferred.

This invention has been described in this application in considerable detail in order to comply with the patent statutes and to provide those skilled in the art with the information needed to apply the novel principles and to construct any of its subspecialized components as required. However, it is to be further understood that the invention can be carried out by specifically different equipment and devices and at various modifications, both as to equipment details and operating procedures, and can be accomplished without departing from the scope of the invention itself.

What is claimed is:

1. A dental curette, adapted to be held by a hand, comprising:
   (a) a shaft member having a first end and a second end proximate a working head; and
   (b) finger pad means axially constrained and selectively rotatable about said second end proximate said working head for receiving a first finger of said hand, said finger pads means having a first finger-surface complementary contoured to receive said first finger when said dental curette is held by said hand.

2. The dental curette as specified in claim 1 wherein said first finger-surface of said finger pad means is generally concave.

3. The dental curette as specified in claim 2 wherein said first finger-surface tapers toward said working head.

4. The dental curette as specified in claim 2 wherein said second end of said shaft member further comprises stop means for restricting rotation less than 360°.

5. The dental curette as specified in claim 1 wherein said first finger-surface is textured.

6. The dental curette as specified in claim 1 wherein said finger pad means has an arcuate inner surface such that said finger pad means is selectively detachable from said second end.

7. The dental curette as specified in claim 1 wherein said second end of said shaft member includes a restraining means restraining longitudinal sliding of said finger pad means along an axis of said shaft member.

8. The dental curette as specified in claim 1 wherein said finger pad means has a second finger-surface contoured to receive said first finger of said hand.

9. The dental curette as specified in claim 1 wherein said finger pad means has a generally conical shape tapering towards said first working head.

10. The dental curette as specified in claim 1 wherein said finger pad means is comprised of a resilient material.

11. The dental curette as specified in claim 10 wherein said resilient material comprises plastic.

12. The dental curette as specified in claim 10 wherein said resilient material comprises a rubber material.

13. The dental curette as specified in claim 1 wherein said finger pad means comprises sterilizable material.

14. The dental curette as specified in claim 1 wherein said finger pad means is comprised of a flexible material.

15. A dental curette adapted to be held by a hand comprising:
   (a) a shaft member having a first hand held end and a second end, said second end having a tapered region tapering to a sharpened member; and
   (b) finger pad means coaxially disposed about and substantially covering said tapered region for receiving a first finger, said finger pad means having a substantially straight opening defined therethrough receiving and closely conforming to said tapered region of said shaft member.

16. The dental curette as specified in claim 15 wherein said tapered region of said second end further comprises restraining means for restraining lateral sliding of said finger pad means along an axis of said shaft member.

17. The dental curette as specified in claim 15 wherein said finger pad means is sterilizable.

18. The dental curette as specified in claim 15 wherein said finger pad means has a cylindrical symmetric cross section.

19. The dental curette as specified in claim 18 wherein said finger pad means is generally cylindrical having a diameter substantially equal to a diameter of said shaft member.

20. The dental curette as specified in claim 19 wherein said finger pad means comprises a resilient tubular sleeve.

21. The dental curette as specified in claim 15 wherein said finger pad means is generally oval.

22. The dental curette as specified in claim 15 wherein said finger pad means is selectively rotatable about said tapered region, said finger pad means having a first finger-surface complementary contoured to receive said first finger of said hand.

23. The dental curette as specified in claim 22 wherein said finger pad means has a second finger-surface contoured to receive said first finger of said hand.

* * * * *